(12) United States Patent
Gorton et al.

(10) Patent No.: US 7,118,689 B2
(45) Date of Patent: Oct. 10, 2006

(54) STABILIZED POLYCHLOROETHYLENES

(75) Inventors: Earl M. Gorton, Sulphur, LA (US); Ronald D. Olinger, Lake Charles, LA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 398 days.

(21) Appl. No.: 10/648,970

(22) Filed: Aug. 27, 2003

(65) Prior Publication Data

US 2005/0049442 A1  Mar. 3, 2005

(51) Int. Cl.
- F01M 1/16 (2006.01)
- F16N 7/36 (2006.01)
- F16N 25/04 (2006.01)

(52) U.S. Cl. ............ 252/401; 252/403; 570/109; 570/264; 523/310

(58) Field of Classification Search ......... 523/310; 524/99, 102; 252/401, 403; 570/109, 264
See application file for complete search history.

(56) References Cited

U.S. PATENT DOCUMENTS

| | | | |
|---|---|---|---|
| 2,492,048 A * | 12/1949 | Klabunde | 570/109 |
| 3,251,891 A | 5/1966 | Cormany et al. | |
| 3,265,747 A | 8/1966 | Cormany et al. | |
| 3,281,480 A | 10/1966 | Hardies et al. | |
| 3,494,967 A | 2/1970 | Bailey | 260/652.5 |
| 3,499,047 A | 3/1970 | Cormany et al. | |
| 3,532,761 A | 10/1970 | Manner et al. | |
| 3,535,392 A | 10/1970 | Cormany et al. | |
| 3,733,326 A | 5/1973 | Murayama et al. | 260/290 V |
| 4,001,345 A | 1/1977 | Gorton et al. | |
| 4,018,837 A | 4/1977 | Archer et al. | |
| 4,046,820 A | 9/1977 | Goodner et al. | |
| 4,069,265 A | 1/1978 | Richtzenhain et al. | |
| 4,088,629 A * | 5/1978 | Uhrhan et al. | 524/99 |
| 4,309,301 A | 1/1982 | Ishibe et al. | |
| 4,324,928 A | 4/1982 | Pryor et al. | |
| 4,351,973 A | 9/1982 | Ishibe et al. | |
| 4,404,412 A | 9/1983 | Ishibe et al. | 570/109 |
| 4,416,797 A * | 11/1983 | Minagawa et al. | 252/400.1 |
| 4,992,604 A | 2/1991 | Reich et al. | |
| 5,405,891 A | 4/1995 | Pitteloud | |
| 5,449,724 A * | 9/1995 | Moffat et al. | 526/204 |
| 5,654,430 A | 8/1997 | Pitteloud | |
| 6,040,488 A * | 3/2000 | Amato et al. | 570/264 |
| 6,150,573 A | 11/2000 | Taylor et al. | |
| 6,156,858 A * | 12/2000 | Keoshkerian et al. | 526/204 |
| 6,500,982 B1 | 12/2002 | Hale et al. | 562/600 |

FOREIGN PATENT DOCUMENTS

| | | |
|---|---|---|
| EP | 0 845 458 A1 | 6/1998 |
| JP | 09-328444 | 12/1997 |
| WO | WO 98/02400 | 1/1998 |

OTHER PUBLICATIONS

Copending U.S. Appl. No. 10/436,664, Method of Stabilizing Trichloroethane During Production, filed May 13, 2003.
Copending U.S. Appl. No. 10/648,976, Method of Stabilizing Tetrachloroethylene During Production, filed Aug. 27, 2003.
Kirk-Othmer Encyclopedia of Chemical Technologh, 3$^{rd}$ Ed., vol. 23; John Wiley & Sons, NY (1983), p. 868.
Kirk-Othmer Encyclopedia of Chemical Technologh, 3$^{rd}$ Ed., vol. 17; John Wiley & Sons, NY (1982), pp. 1-90.
Ciba Product Bulletin PROSTAB 5198, Mar. 1999.
Ciba Product Bulletin PROSTAB 5415, Dec. 1999.
Copending U.S. Appl. No. 10/648,972, Stabilized Trichloroethane, filed Aug. 27, 2003.

* cited by examiner

Primary Examiner—Kriellion Sanders
(74) Attorney, Agent, or Firm—Linda Pingitore

(57) ABSTRACT

Polychloroethylene, e.g., trichioroethylene and perchloroethylene, is stabilized with a stabilizing amount of a stable free radical stabilizer, e.g., a material having the 2,2,6,6-tetra (lower alkyl)-1-piperidinyloxy-yl free radical group, such as 2,2,6,6-tetramethyl-4-hydroxy-1-piperidinyloxy, or the 2,2, 5,5-tetra(lower alkyl)pyrrolidinyloxy group, such as 2,2,5, 5-tetramethyl pyrrolidinyloxy. Stable free radical stabilizer is removed from a polychloroethylene composition containing same by contacting the composition with silica, e.g., precipitated silica.

18 Claims, No Drawings

STABILIZED POLYCHLOROETHYLENES

DESCRIPTION OF THE INVENTION

The present invention relates to the stabilization of polychloroethylenes. In particular, this invention relates to the stabilization of polychloroethylenes, such as trichloroethylene and perchloroethylelle during storage and shipment. More particularly, this invention relates to polychloroetlhylenes containing a stabilizing amount of a stable free radical stabilizer, e.g., a material having a 2,2,6,6-tetra(lower alkyl)-1-piperidinyloxy-yl free radical group.

Other than in any operating examples, or where otherwise indicated, all numbers expressing quantities that are used in this specification and the accompanying claims are to be understood as modified in all instances by the term "about".

DETAILED DESCRIPTION OF THE INVENTION

Polychloroethylenes, particularly trichloroethylene and perchloroethylene, have been used as solvents in many different technical processes, e.g., in the degreasing of metals, in the extraction of oils and fats, in the dry cleaning of fabrics., etc. When subjected to the effects of heat, oxygen, light and water, these polychloroethylenes tend to decompose and form acid products such as hydrochloric acid. dichloroacetic acid, phosgene, tarry substances and the like. These decomposition products can cause problems during storage and during transportation, as well as during their use in the aforedescribed technical processes and during their recovery after use. The decomposition of these polychloroethylenes is accelerated by the presence of metals or metal salts, as well as by the direct and indirect products of the decomposition itself, and is autocatalytic.

The aforesaid decomposition process is particularly troublesome in connection with the degreasing of metals, particularly metals containing iron or aluminum, where because of the conditions present during the degreasing process, e.g., heat, oxygen, humidity and the metal itself, considerable decomposition of the polychloroethylene can occur.

It has been proposed to stabilize these polychloroethylenes by adding singly or in combination a plethora of various stabilizing compounds. Examples of such stabilizing compounds can be found in the patent literature and include phenols, aliphatic epoxides, alcohols, tertiary amines, aliphatic nitriles, hydrazones, hydroznes, pyrroles, glycidol, epichlorohydrin, epibromohydrin, oximes of lower alkanols, etc. Some of such stabilizer materials are intended to stabilize either the vapor or liquid form of the polychloroethylene, or in some cases to stabilize both the vapor and liquid form, depending on the use for which the polychloroethylene is intended. Some stabilizer materials reduce the susceptibility of polychloroethylene to metal induced decomposition, while others serve as an acceptor for the acid, e.g., hydrochloric acid, that is produced during decomposition.

More recently, these polychloroethylenes have been proposed for use as feed stocks for the preparation of other halogenated hydrocarbons, such as chloro-fluoro hydrocarbons. For this use, it is desirable to have a chemical stabilizer or chemical stabilization system that does not interfere with the catalyst used to produce the other halogenated hydrocarbons, e.g., chloro-fluoro hydrocarbons, such as by deactivating the catalyst, and/or a chemical stabilizer or stabilization system that can be readily removed from the polychloroethylene, e.g., by distillation or adsorption on an inert substrate.

Accordingly, it is an object of the present invention to provide a new and effective chemical stabilizer or chemical stabilization system for polychlioroethylenes, particularly trichloroethylene and perchloroethylene, the latter of which is sometimes referred to as "Perc". In one embodiment of the present invention, the polychloroethylenes can be represented by the following graphic formula,

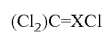

$(Cl_2)C=XCl$ wherein X is hydrogen or chlorine. When X is hydrogen, formula I depicts trichloroethylene, and when X is chlorine, formula I depicts tetrachloroethylene or perchloroethylene, as it is commonly called. As used in this disclosure, the terms tetrachloroethylene and perchloroethylene are used interchangeably.

It has now been surprisingly discovered that polychloroethylenes. e.g., those depicted by formula I, can be stabilized against decomposition, e.g., air oxidation, during storage and transportation by the presence of a stabilizing amount of a stable free radical material. An example of a type of stable free radical found to be particularly effective is a material characterized as having at least one 2,2,6,6-tetra(lower alkyl)-1-piperidinyloxy-yl free radical group. Moreover, it is contemplated that such free radical stabilizer will not adversely affect, e.g., deactivate, catalysts used by manufacturers that use these polychloroethylenes as feed stocks in the production of fluorinated hydrocarbons, e.g., chlorofluoro hydrocarbons.

As is known in the art, trichloroethylene and perchloroethylene can be produced by the catalytic oxychlorination of ethylene or dichloroethane. The oxychlorination reaction is exothermic and is carried out at temperatures in the range of 425° C. and pressures of from 138 to 207 kPa (20 to 30 psi). Common catalysts used are mixtures of potassium and cupric chlorides. The oxychlorination reaction temperature is controlled by techniques known to those skilled in the art, e.g., by use of a fluidized bed. The ratio of trichloroethylene to perchloroethylene in the crude product can be varied to some degree by adjusting the mole feed ratios of dichloroethane, chlorine and oxygen.

After vent scrubbing, the condensed crude trichloroethylene/perchloroethylene product and the weak hydrochloric acid by-product are separated, and the crude product is dried by azeotropic distillation. Distillation of the trichloroethylene-perchloroethylene crude product splits the crude product into two streams, one rich in trichloroethylene and the other rich in perchloroethylene. Perchloroethylene and components with boiling points higher than perchloroethylelle (heavies) are fed to a distillation column. The overhead from this column is fed to the perchloroethylene distillation column. The bottoms from this column is neutralized with ammonia, washed and dried. See, for example, Kirk-Othmer Encyclopedia of Chemical Technology, third edition, Volume 5, pages 745 to 762, John Wiley & Sons, New York (1983).

An example of stable free radical stabilizer material that can be used to stabilize polychloroethylenes is a material that has at least one 2,2,6,6-tetra(lower alkyl)-1-piperidinyloxy-yl free radical group. The lower alkyl groups can be the same or they may be different, but usually they will be the same, and will comprise from 1 to 5, e.g., 1 to 4, carbon atoms. The lower alkyl group usually employed is methyl or ethyl, although lower alkyl groups having more than two carbon atoms, e.g., three or four carbon atoms, are contemplated. Typically, the lower alkyl group is methyl.

The 2,2,6,6-tetra(lower alkyl)-1-piperidinyloxy-yl free radical group is usually the 2,2,6,6-tetra(lower alkyl)-1-piperidinyloxy-4-yl free radical group, but the 2,2,6,6-tetra (lower alkyl)-1-piperidinyloxy-3-yl free radical group may be used, if desired. The 2,2,6,6-tetra(lower alkyl)-1-piperidinyloxy-yl free radical group can be attached, for example, to hydrogen, hydroxyl, oxo, or to a parent compound as a substituent. In those embodiments in which the stable free radical is substituted onto a parent compound, the typical parent compound is a monocarboxylic acid or a dicarboxylic acid, in which case the stable free radical stabilizer material is an ester. The monocarboxylic acids can be aliphatic or aromatic. In one contemplated embodiment, the aliphatic monocarboxylic acid is saturated and contains from 1 to 18 carbon atoms. In other contemplated embodiments, the aliphatic monocarboxylic acid contains from 2 to 12 carbon atoms e.g., from 3 to 8 carbon atoms. Of the aromatic monocarboxylic acids, benzoic acid is a particular embodiment. When dicarboxylic acids are used as the parent compound, the dicarboxylic acids can be saturated and contain from 2 to 13 carbon atoms. In one contemplated embodiment, the saturated dicarboxylic acid contains from 4 to 12 carbon atoms, e.g., from 8 to 12 carbon atoms. A particular contemplated embodiment of a saturated dicarboxylic acid is sebacic acid, which contains 10 carbon atoms. It should be understood that the stable free radical material of the present invention need not be associated with a parent compound, and in certain embodiments of the present invention, the stable free radical material itself is used.

Stable free radicals described herein and methods for their preparation are known to those skilled in the art. Non-limiting examples of suitable free radical materials that can be used in the present invention include:

2,2,6,6-tetramethyl-1-piperidinyloxy [CAS 2564-83-2];
2,2,6,6-tetramethyl-4-hydroxy-1-piperidinyloxy [CAS 2226-96-2] having the structure:

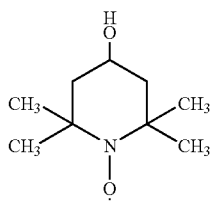

which material is also known as 4-hydroxy-TEMPO, and which is commercially available as a 5% active ingredient in an inert solvent mix from GE Betz as PETROFLO 20Y104, and which is also available in solid form from Ciba Specialty Chemicals as PROSTAB 5198;

2,2,6,6-tetramethyl-4-oxo-1-piperidinyloxy [CAS 2896-70-0];
2,2,6,6-tetramethyl-4-amino-piperidinyloxy;
2,2,6,6-tetramethyl-4-dimethylamino-piperidinyloxy;
2,2,6,6-tetramethyl-4-ethanoyloxy piperidinyloxy;
2,2,6,6-tetramethyl-4-((methylsulfonyl)oxy)-1-piperidinyloxy [CAS 35203-66-8];
2,2,6,6-tetramethyl-1-piperidinyloxy-4-yl benzoate [CAS 3225-26-1]; and
bis(2,2,6,6-tetramethyl-1-piperidinyloxy-4-yl) sebacate [CAS 2516-92-9], which is available commercially in solid form, and as a 4 to 10% solution in an organic solvent from Ciba Specialty Chemicals as PROSTAB 5415.

Other examples of stabilizer materials that are contemplated for use as a stabilizer for polychloroethylenes include materials having a 2,2,5,5-tetra(lower alkyl)pyrrolidinyloxy group. As in the case of the 2,2,6,6-tetra(lower alkyl)-1-piperidinyloxy-yl group described heretofore, the lower alkyl groups can be the same or different, but usually will be the same, and will comprise from 1 to 5, e.g., 1 to 4, carbon atoms. The lower alkyl group usually employed is methyl or ethyl. Typically, the lower alkyl group is methyl, i.e., 2,2,5,5-tetramethyl pyrrolidinyloxy. Non-limiting examples of such stabilizer materials include:

2,2,5,5-tetramethyl-pyrrolidinyloxy;
3-amino-2,2,5,5-tetramethyl-pyrrolidinyloxy;
2,2,5,5-tetramethyl-1-oxa-3-azacyclopentyl-3-oxy; and
2,2,5,5-tetramethyl-3-pyrrolinyl-1-oxy-3-carboxylic acid.

The amount of stable free radical stabilizer additive that is used to stabilize polychloroethylenes, as described herein, can vary. In general, the amount of stable free radical stabilizer additive used can be characterized as a stabilizing amount. It is contemplated that at least one stable free radical stabilizer material, such as the free radical stabilizer materials described above, derivatives thereof, or equivalents of such stabilizer materials or derivatives thereof can be used. The amount of stable free radical additive added to the polychloroethylene compound will also depend upon the degree of stability desired and the effectiveness of the particular stable free radical employed. Minimal amounts may yield de minimis improvements. On the other hand diminishing returns are generally encountered when using amounts significantly larger than the amounts that provide an economically effective deterrent to air induced decomposition, i.e., the formation of undesired levels of contaminating decomposition products. The upper and lower limits of practical effectiveness can be readily determined by one skilled in the art by measuring the amounts of decomposition products in the polychloroethylelle as the amount of stable free radical stabilizer added to the polychloroethylene is varied. Another useful method for measuring the effectiveness of the free radical stabilizer and the amounts thereof used is to measure over time the pH of polychloroethylene containing various amounts of stable free radical stabilizer.

It is contemplated that stable free radical stabilizer will be present in amounts of at least one (1) part per million parts (ppm) of polychloroethylene, e.g., trichloroethylene or tetrachloroethylene, e.g., from 1 to 25 ppm. In a particular contemplated embodiment, it is contemplated that from 2 ppm to 15 ppm, of stable free radical stabilizer is used. The amount of stable free radical stabilizer used can vary in amounts ranging between any of the aforedescribed upper and lower values, inclusive of the recited values.

As stated earlier, stabilization of polychloroethylenes can be measured by measuring the pH (acidity) over time of the polychloroethylene with and without use of one or more stable free radical stabilizers. The following method for determining the pH of trichloroethylene can be used, which method was the method followed in Example 1:

Add 75 milliliters (mL) of reagent water containing sodium chloride to a 250 mL glass beaker, and adjust the pH of the water to 7.0 with 0.01 N sodium hydroxide or 0.01 N hydrochloric acid. The reagent water is prepared by adding 0.2 to 0.4 grams of sodium chloride salt to approximately 900 mL of distilled water. This salt solution is boiled vigorously to remove carbon dioxide. After boiling the solution is stoppered and allowed to cool.

Add 25±0.1 mL of the trichloroethylene sample into the 250 mL glass beaker and stir the mixture rapidly for at least 1 minute. Discontinue stirring and allow the aqueous and organic phases to separate. Read the pH of the aqueous phase with a pH meter, e.g., a Thermo-Orion pH meter or equivalent.

The following method for measuring the pH of perchloroethylene can be used, which method was the method followed in Example 2:

Add 100 mL of the polychloroethylene sample into a 250 mL separatory funnel with a ground glass stopper. Add 25±0.1 mL of reagent water (described above), the pH of which has been adjusted to 7.0 with either 0.01 N sodium hydroxide or 0.01 N hydrochloric acid, to the separatory funnel. Stopper and shake the separatory funnel for 2 minutes. After the mixture has separated into two phases, separate the bottom organic phase and add the aqueous phase into a 50 mL beaker. Stir the aqueous phase for a minimum of 30 seconds and measure the pH of the aqueous phase. e.g., with a Thermo-Orion pH meter or equivalent.

It has also been discovered that the stable free radical stabilizer added to polychloroethylene to stabilize it against air oxidation during storage and shipment can be removed by contacting the stabilized polychloroethylene with silica, e.g., precipitated silica, silica gel and fumed silica. For economic reasons, it is contemplated that precipitated silica will typically be used. Removal of the stable free radical stabilizer from the polychloroethylene, e.g., trichloroethylene and perchloroethylene, may be desirable when these materials are used as a feed stock for the production of other halogenated compounds, e.g., fluorinated hydrocarbons or fluoro-chloro hydrocarbons, and a very pure polychloroethylene feed stock is required.

The amount of silica required will, of course, vary and will depend on the amount of free radical stabilizer used with the Polychloroethylene and the adsorptive capacity of the particular silica used. Typically, an amount of silica that is sufficient to adsorb substantially all of the free radical stabilizer material in the polychloroethylene composition is used. Generally, the polychloroethylene will contain minor amounts of free radical stabilizer, e.g., less than 50 ppm, more usually not more than 25 ppm. It is contemplated that at least 0.05, e.g., at least 0.1 weight percent, of silica, such as precipitated silica, (based on the polychloroethylene treated) will be sufficient to remove (adsorb) substantially all of the stable free radical stabilizer from the polychloroethylene liquid composition comprising the polychloroethylene and the minor amount of free radical stabilizer, thereby to provide a polychloroethylene that is substantially free of stable free radical stabilizer.

Treatment of the polychloroethylene with the silica can be performed by any convenient method and in any conventional equipment that is used to bring a liquid and solid into intimate contact. It is contemplated that the treatment will be performed under ambient conditions, and under conditions that prevents the polychloroethylene from coming into significant contact with air or other destabilizing conditions, e.g., contact with water, metals, metal halides etc.

The present invention is further described in the following examples, which are to be considered as illustrative, rather than limiting, of the invention, and wherein all parts are parts by weight and all percentages are percentages by weight unless specified otherwise.

EXAMPLE 1

A stock solution of PROSTAB® 5415 stabilizer in trichloroethylene was prepared in the following manner:

0.49 grams of PROSTAB® 5415 stabilizer was added to a one quart amber bottle, which was then filled with 1329.1 grams of commercially produced unstabilized trichloroethylene obtained from the trichloroethylene commercial production unit of PPG Industries, Inc. located at Lake Charles, La. The concentration of PROSTAB® 5415 in the trichloroethylene stock solution was calculated to be 368.7 parts per million parts (ppm) of trichloroethylene. The pH of the trichloroethylene, as collected from the commercial unit, had a pH of 6.7. Trichloroethylene from this commercial unit typically has an assay of 99.99% trichloroethylene.

Test samples were prepared from the standard solutions by adding 5, 10, 20 and 30 milliliters (ml) of the standard solution respectively to four one quart amber bottles, which were then filled with the same unstabilized trichloroethylene used to prepare the standard solution. The level of PROSTAB® 5415 in each of the four quart bottles was calculated to be 2.11, 4.15, 8.36 and 12.88 ppm respectively. These bottles were designated with the sample numbers 1, 2, 3, and 4 respectively.

A fifth quart bottle was filled with the same unstabilized trichloroethylene used to prepare the aforedescribed four test samples and was identified as sample number 5. No PROSTAB® 5415 stabilizer was added to this fifth bottle, which was used as a control sample. The control sample was stoppered and stored in a laboratory oven maintained at 120° F. (48.8° C.). No precautions were made to exclude air. The pH of the trichloroethylene in the control sample (sample number 5) was measured within 12 hours of being collected from the production unit and placed in the laboratory oven. The sample smelled of acid chlorides and had a pH of 3.9.

The four test samples containing the PROSTAB® 5415 stabilizer were also stoppered and stored in a laboratory oven maintained at 120° F. (48.8° C.). No precautions were made to exclude air. At approximately 7-day intervals, the pH of the test samples was measured. The pH measurements obtained are tabulated in Table 1.

TABLE 1

| | pH of Test Solution | | | |
|---|---|---|---|---|
| | Test Solution Number | | | |
| Elapsed Time (days) | 1 | 2 | 3 | 4 |
| 6 | 6.6 | 6.8 | 6.7 | 6.8 |
| 13 | 6.8 | 6.8 | 6.8 | 6.8 |
| 20 | 6.9 | 6.5 | 6.5 | 6.3 |
| 27 | 6.5 | 6.7 | 6.7 | 6.8 |
| 34 | 6.6 | 6.7 | 6.7 | 6.7 |
| 42 | 6.3 | 6.2 | 6.2 | 6.2 |
| 48 | 6.2 | 6.2 | 6.2 | 6.3 |
| 55 | 6.1 | 6.3 | 6.3 | 6.3 |
| 62 | 6.3 | 6.4 | 6.4 | 6.5 |
| 83 | 6.3 | 6.3 | 6.3 | 6.3 |
| 90 | 6.5 | 6.4 | 6.3 | 6.4 |
| 98 | 6.4 | 6.3 | 6.3 | 6.5 |
| 105 | 6.5 | 6.4 | 6.4 | 6.4 |
| 165 | 6.6 | 6.6 | 6.7 | 6.7 |

The data of Table 1 shows that trichloroethylene can be stabilized by use of a stable free radical stabilizer, as demonstrated by the fairly constant pH levels of the test samples over a period of approximately 23.5 weeks; whereas, unstabilized trichloroethylene (control sample)

started to decompose within 12 hours of its collection, which decomposition generated acidic species, as shown by the control sample pH of 3.9 at that time interval.

EXAMPLE 2

A stock solution of PROSTAB® 5415 stabilizer in perchloroethylene was prepared in the following manner:

0.52 grams of PROSTAB® 5415 was added to a one quart amber bottle, which was then filled with 1440.4 grams of commercially produced unstabilized perchloroethylene obtained from the perchloroethylene commercial production unit of PPG Industries, Inc. located at Lake Charles, La. The concentration of PROSTAB® 5415 in the perchloroethylene was calculated to be 361 parts per million parts of perchloroethylene. The pH of the perchloroethylene, as collected, had a pH of 6.8. Perchloroethylene from this commercial unit typically has an assay of 99.98% perchloroethylene.

Test samples were prepared by adding 5, 10, 15 and 25 milliliters of the stock solution respectively to four one quart amber bottles, which were then filled with the same unstabilized perchloroethylene used to prepare the stock solution. The level of PROSTAB® 5415 in each of the four quart sample bottles was calculated to be 2.24. 4.33, 6.48 and 11.13 ppm respectively. These bottles were designated with the sample numbers 1, 2, 3, and 4 respectively.

A fifth quart amber bottle was filled with the same unstabilized perchloroethylene used to prepare the afore-described four test samples and was identified as sample number 5. No PROSTAB® 5415 stabilizer was added to this fifth bottle. Sample number 5 was used as the control sample. The control sample was stoppered and stored in a laboratory oven maintained at 120° F. (48.8° C.). No precautions were made to exclude air. The pH of the perchloroethylene in the control sample was tested within 12 hours of being collected from the production unit and placed in the laboratory oven and found to have a pH of 3.9.

The four test samples containing the PROSTAB® 5415 stabilizer were also stoppered and stored in a laboratory oven maintained at 120° F. (48.8° C.). No precautions were made to exclude air. At various intervals (4 to 7 days), the pH of the test samples was measured. The pH measurements obtained are tabulated in Table 2.

TABLE 2

| | pH of Test Sample | | | |
| --- | --- | --- | --- | --- |
| | Test Sample Number | | | |
| Elapsed Time (days) | 1 | 2 | 3 | 4 |
| 6 | 6.6 | 6.2 | 6.4 | 6.0 |
| 11 | 6.2 | 6.1 | 6.3 | 6.4 |
| 17 | 6.4 | 6.4 | 6.5 | 6.4 |
| 21 | 7.1 | 7.1 | 7.1 | 7.1 |
| 28 | 6.5 | 6.4 | 6.4 | 6.3 |
| 35 | 6.8 | 6.7 | 6.3 | 6.5 |
| 42 | 7.0 | 7.1 | 7.1 | 7.1 |
| 49 | 7.1 | 6.9 | 7.1 | 7.0 |

The data of Table 2 shows that perchloroethylene can be stabilized by use of a free radical stabilizer, as demonstrated by the fairly constant pH levels over a period of 7 weeks; whereas, unstabilized perchloroethylene (control sample) started to decompose within 12 hours of its collection, which decomposition generated acidic species, as shown by the sample pH of 3.9 at that time interval.

Although the present invention has been described with reference to specific details of certain embodiments thereof, it is not intended that such details should be regarded as limitations upon the scope of the invention except insofar as they are included in the accompanying claims.

What is claimed is:

1. A method for removing stable free radical stabilizer from a liquid composition comprising polychloroethylene and a minor amount of stable free radical stabilizer, comprising contacting said liquid composition with an amount of silica sufficient to adsorb stable free radical stabilizer and provide a polychloroethylene composition substantially free of stable free radical stabilizer.

2. The method of claim 1 wherein the polychloroethylene is trichloroethylene or perchloroethylene.

3. The method of claim 2 wherein the silica is precipitated silica, silica gel or fumed silica.

4. The method of claim 3 wherein the free radical stabilizer is present in amounts of at least 1 part per million parts of polychloroethylene.

5. The method of claim 4 wherein the free radical stabilizer is a material having the 2,2,6,6-tetra(lower alkyl)-1-piperidinyloxy-yl free radical group.

6. The method of claim 5 wherein the 2,2,6,6-tetra(lower alkyl)-1-piperidinyloxy-yl free radical group is the 2,2,6,6-tetramethyl-1-piperidinyloxy-yl free radical group.

7. The method of claim 4 wherein the stable free radical stabilizer is a material having the 2,2,6,6-tetra(lower alkyl)-1-piperidinyloxy-4-yl free radical group.

8. The method of claim 7 wherein the stable free radical stabilizer is a material having the group 2,2,6,6-tetramethyl-4-hydroxy-1-piperidinyloxy, 2,2,6,6-tetramethyl-4-amino-piperidinyloxy, 2,2,6,6-tetramethyl-4-dimethylamino-piperidinyloxy, 2,2,6,6-tetramethyl-4-ethanoyloxy piperidinyloxy, 2,2,6,6-tetramethyl-4-oxo-1-piperidinyloxy, 2,2,6,6-tetramethyl-4-((methylsulfonyl)oxy)-1-piperidinyloxy, or 2,2,6,6-tetramethyl-1-piperidinyloxy-4-yl benzoate.

9. The method of claim 7 wherein the stable free radical stabilizer is bis(2,2,6,6-tetramethyl-1-piperidinyloxy-4-yl) ester of saturated dicarboxylic acid.

10. The method of claim 9 wherein the saturated dicarboxylic acid contains from 2 to 13 carbon atoms.

11. The method of claim 9 wherein the stable free radical stabilizer is bis(2,2,6,6-tetramethyl-1-piperidinyloxy-4-yl) sebacate.

12. The method of claim 4 wherein the free radical stabilizer is a material having the 2,2,6,6-tetramethyl-4-hydroxy-1-piperidinyloxy group, which material is present in amounts of from 2 to 15 parts per million parts of polychloroethylene.

13. A composition comprising polychloroethylene chosen from trichloroethylene and perchloroethylene and a stabilizing amount of stable free radical stabilizer having the 2,2,5,5-tetra(lower alkyl)pyrrolidinyloxy group.

14. The composition of claim 13 wherein the 2,2,5,5-tetra (lower alkyl)pyrrolidinyloxy group is 2,2,5,5-tetramethyl pyrrolidinyloxy and the free radical stabilizer is present in amounts of at least 1 part per million parts of polychloroethylene.

15. The composition of claim 14 wherein the free radical stabilizer is a material having the group 2,2,5,5-tetramethyl-3-amino-pyrrolidinyloxy, 2,2,5,5-tetramethyl-1-oxa-3-aza-cyclopentyl-3-oxy, or 2,2,5,5-tetramethyl-3-pyrrolinyl-1-oxy-3-carboxylic acid.

16. A method for removing stable free radical stabilizer from a liquid composition comprising polychloroethylene and less than 50 ppm of stable free radical stabilizer having the 2,2,6,6-tetra(lower alkyl)-1-piperidinyloxy-yl free radical group, comprising treating said liquid composition with an amount of precipitated silica sufficient to adsorb stable free radical stabilizer and provide a polychloroethylene composition substantially free of stable free radical stabilizer.

17. The method of claim 16 wherein the polychloroethylene is trichloroethylene or perchloroethylene, and the 2,2,6,6-tetra(lower alkyl)-1-piperidinyloxy-yl free radical group is the 2,2,6,6-tetramethyl-1-piperidinyloxy-yl free radical group.

18. The method of claim 17 wherein the precipitated silica is used in an amount of at least 0.05 weight percent, based on the liquid polychloroethylene composition treated.

* * * * *